United States Patent
Solotoff (10) Patent No.: US 11,602,451 B1
(45) Date of Patent: Mar. 14, 2023

(54) SHOULDER SLING WITH AIR ABDUCTION PAD

(71) Applicant: PREFERRED PRESCRIPTION, INC., Hollywood, FL (US)

(72) Inventor: Brandon Solotoff, Boca Raton, FL (US)

(73) Assignee: Preferred Prescription, Inc., Hollywood, FL (US)

( * ) Notice: Subject to any disclaimer, the term of this patent is extended or adjusted under 35 U.S.C. 154(b) by 220 days.

(21) Appl. No.: 16/908,961

(22) Filed: Jun. 23, 2020

Related U.S. Application Data (60) Provisional application No. 62/867,394, filed on Jun. 27, 2019, provisional application No. 62/890,204, filed on Aug. 22, 2019, provisional application No. 62/909,287, filed on Oct. 2, 2019.

(51) Int. Cl.
*A61F 5/37* (2006.01)

(52) U.S. Cl.
CPC .......... *A61F 5/3753* (2013.01); *A61F 5/3738* (2013.01)

(58) Field of Classification Search
CPC .... A61F 5/3723; A61F 5/3738; A61F 5/3753; A61F 5/373; A61F 5/05858
USPC .......................................................... 602/4
See application file for complete search history.

(56) References Cited

U.S. PATENT DOCUMENTS

| | | |
|---|---|---|
| 795,108 A | 7/1905 | Doellinger |
| 1,304,153 A | 5/1919 | Bugge |
| 2,875,754 A | 3/1959 | Messer |
| 3,404,680 A | 10/1968 | Gutman |
| 3,872,525 A | 3/1975 | Lea |
| 4,372,301 A | 2/1983 | Hubbard |
| 4,622,961 A | 11/1986 | Christensen |
| 4,716,895 A | 1/1988 | Marques |

(Continued)

FOREIGN PATENT DOCUMENTS

EP 1 645 251 12/2006

OTHER PUBLICATIONS

Press Fit Forces Stress Design Calculator, Jun. 18, 2018, available at: www.engineersedge.com/calculators/machine-design/press-fit/press-fit.htm.

(Continued)

*Primary Examiner* — Camtu T Nguyen
(74) *Attorney, Agent, or Firm* — Thomas A. O'Rourke; Bodner & O'Rourke, LLP (57) ABSTRACT

A sling includes a strap assembly, and arm support cushion that includes: an inflatable bladder, valve, and hand-squeezable pump. The bladder has first and second surfaces corresponding to contours of the wearer's torso and arm, respectively. The valve permits air flow into or out from the bladder. The resilient bulb-shaped pump is squeezed to inflate the bladder, through the valve being in fluid communication with a hose, providing greater reach of the hand pump for each of the wearer's left/right hands. Alternatively, the bladder has first and second valves positioned on first and second sides of the bladder permitting left/right-handed use of the pump. The bladder's interior includes high-inflation foam to suck air therein to increase a rate of inflation of the bladder from a deflated condition. Decoupling of the resilient pump permits repetitive squeezing as exercise by the user. and/or blowing of air onto the wearer's arm.

8 Claims, 9 Drawing Sheets

(56) References Cited

U.S. PATENT DOCUMENTS

| | | | |
|---|---|---|---|
| 4,834,082 A | 5/1989 | Ghadiali | |
| 4,896,660 A | 1/1990 | Scott | |
| 5,334,132 A | 8/1994 | Burkhead | |
| 5,348,530 A * | 9/1994 | Grim | A61F 5/0111 602/5 |
| 5,423,333 A | 6/1995 | Jensen | |
| 5,464,383 A | 11/1995 | Padden | |
| 5,514,081 A | 5/1996 | Mann | |
| 5,569,172 A * | 10/1996 | Padden | A61F 5/3753 602/20 |
| 5,776,105 A * | 7/1998 | Corn | A61M 5/1483 604/179 |
| 5,865,166 A | 2/1999 | Fitzpatrick | |
| 6,511,449 B2 | 1/2003 | Burns | |
| 6,659,971 B2 | 12/2003 | Gaylord | |
| 6,932,781 B2 | 8/2005 | Itoi | |
| 7,300,410 B1 | 11/2007 | Weber | |
| 7,320,669 B2 | 1/2008 | Campbell | |
| 7,563,236 B2 | 7/2009 | Kazmierczak | |
| 8,016,780 B1 * | 9/2011 | Sickles | A61F 5/3715 602/5 |
| 8,192,382 B2 | 6/2012 | Huang | |
| 8,286,285 B2 | 10/2012 | Mahler | |
| 8,414,512 B2 | 4/2013 | Fout | |
| 9,204,984 B2 | 12/2015 | Brown | |
| 9,265,643 B2 | 2/2016 | Britt | |
| 10,507,130 B1 * | 12/2019 | Strasburger | A61F 5/34 |
| 2008/0313813 A1 * | 12/2008 | Adiri | A47D 13/083 5/655 |
| 2009/0119845 A1 | 5/2009 | Bastien | |
| 2012/0246991 A1 * | 10/2012 | Seuk | F41C 33/001 42/94 |
| 2018/0221192 A1 * | 8/2018 | Strasburger | A61F 5/3738 |

OTHER PUBLICATIONS

"Three General Types of Fit," available at www.mmto.org/dclark/Reports/Encoder%20Upgrade/fittolerences%20%5BRead-Only%5D.pdf., Jul. 8, 2019.
"Engineering Fit," available at: https://en.wikipedia.org/wiki/Engineering_fit, Jul. 8, 2019.

* cited by examiner

SHOULDER SLING WITH AIR ABDUCTION PAD

CROSS REFERENCES TO RELATED APPLICATIONS

This application claims priority on U.S. Provisional Application Ser. No. 62/867,394, filed on Jun. 27, 2019, U.S. Provisional Application Ser. No. 62/890,204, filed on Aug. 22, 2019, and U.S. Provisional Application Ser. No. 62/909,287, filed on Oct. 2, 2019, all disclosures of which are incorporated herein by reference.

FIELD OF THE INVENTION

The present invention relates to shoulder slings and the foam cushion used with an arm sling, and more particularly relates to an improved cushion that may be used to support the wearer's arm when using a sling, so as to be more light-weight, easy to use, and provide additional functionality.

BACKGROUND OF THE INVENTION

There are many different types of injuries to a person's wrist, arm, and/or shoulder that may require the use of a sling, to assist in keeping those body parts immobile while healing occurs. Such injuries include, but are not limited to, fractures to the shoulder, arm, elbow or wrist; a surgical procedure such as a surgery to repair a torn rotator cuff; a stroke that may have caused paralysis to a limb; joint dislocations; etc.

A basic arm/shoulder sling typically includes a strap that runs along the person's back, over their shoulder, and down his/her front side, and which strap is secured to at least two locations on apparatus that supports and cradles the wearer's arm. For certain early shoulder slings, such as the one shown by the 1965 U.S. Pat. No. 3,404,680 to Gutman, the apparatus that contacted and supported the arm was merely a pair of other straps that loop around the arm. For other slings, the apparatus that contacted and supported the arm was a cloth pouch (see e.g., U.S. Pat. No. 1,304,153 to Bugge; U.S. Pat. No. 2,875,754 to Messer; U.S. Pat. No. 4,622,961 to Christensen; U.S. Pat. No. 4,372,301 to Hubbard; and U.S. Pat. No. 4,834,082 to Ghadiali.

However, for certain injuries, the arm is preferably immobilized at a particular angle to the wearer's body—a particular abduction, extension, and/or rotation angle. In these instances a patient is required to wear a particular sling arrangement that includes a specially shaped elevation support cushion that maintains the sling-supported limb(s) at the prescribed angle(s). See, for example, U.S. Pat. No. 7,563,236 to Kazmierczak. The elevation support cushion may be integrally formed with the straps of the sling, or may be releasably coupled to the sling or to the wearer. The elevation support cushion is typically made of heavy, space-consuming foam that tends to fatigue the muscles and shoulder of the patient when carried throughout the course of a day, which invariably is required for proper healing of the injury. The fatiguing of the person's muscles and shoulder tend to counter the desired efficacious nature of the wearing of a sling to immobilize the limbs and permit better healing of the tissue.

The present invention seeks to overcome this and other drawbacks of prior art support cushions used in combination with a sling.

It is noted that the citing herein of any patents, published patent applications, or non-patent literature is not an admission as to any of those references constituting prior art with respect to the herein disclosed apparatus.

OBJECTS OF THE INVENTION

It is an object of the invention to provide a cushion for use with a shoulder sling that reduces fatigue to the wearer of the apparatus.

It is another object of the invention to provide a cushion for use with a shoulder sling that is light weight.

It is a further object of the invention to provide a cushion for use with a shoulder sling that is replaces a heavy foam interior with an airfilled bladder.

It is another object of the invention to provide an air-filled bladder cushion for a shoulder sling that supports an arm at a desired abduction, extension, and/or rotation angle.

It is a further object of the invention to provide an air-filled bladder within a cushion for use with a shoulder sling that can be easily folded when not in use.

It is also an object of the invention to provide a hand-squeezable air pump for use with an air-filled bladder forming a cushion for use with a shoulder sling.

If is a further object of the invention to provide a detachable hand-squeezable air pump for an air-filled bladder forming a cushion for a shoulder sling, which detached hand pump can be used to blow air on the limb of the wearer to cool down the arm and reduce sweating.

It is also another object of the invention to provide a detachable hand-squeezable air pump for an air-filled bladder forming a cushion for a shoulder sling, which detached hand pump can be used as a cushioned ball for squeezing by the wearer to exercise his/her muscles.

Further objects and advantages of the invention will become apparent from the following description and claims, and from the accompanying drawings.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

A sling, for use in supporting a wearer's arm, may include: and arm support cushion, and a strap assembly. The arm support cushion may be formed to include: an inflatable bladder, a valve, and a hand-squeezable pump. The inflatable bladder may have a first surface shaped to correspond to the contour of, and to butt up against, the wearer's torso, and a second surface shaped to correspond to the contour of, and to support, the wearer's arm. The valve configured to be actuated to at least first and second position, where the first position only permits air flow in a first direction though the valve, being into the bladder, and the second position permits air flow through the valve in a second direction, being out of the bladder. The hand-squeezable pump is configured to inflate the bladder when squeezed, and may be a resilient, bulb-shaped member, and may be made of synthetic or natural rubber. In one embodiment, the valve may be coupled to and be in fluid communication with a hose, with the hose being in fluid communication with the bladder, to provide greater reach of the hand pump for the user, particularly where one valve may be used. In another embodiment, the hand-squeezable pump is configured to directly coupled to, and be in fluid communication with, the valve, and may be releasably secured thereto, permitting decoupling of the resilient bulb-shaped pump and exercising by the user by squeezing of the bulb-shaped pump, and also blowing of air by the user onto the arm supported by the sling by squeezing of the bulb-shaped pump. In one embodiment, the bladder may have a first valve positioned on a first side of the bladder to permit left-handed use of the hand-squeezable pump when the sling is in use by the wearer; and a second the valve positioned on a second side of the bladder to permit right-handed use of the hand-squeezable pump when the sling is in use by the wearer. The interior of the bladder may include a high-inflation foam configured to suck air into the bladder to increase a rate of inflate of the bladder from a deflated condition. The bladder may also have a first layer of memory foam on the first surface, and a second layer of memory foam on the second surface, to better conform those surface locally to the respective contours of the wearer torso and arm. Water resistant material may be positioned to respectively overlie the first layer of memory foam and the second layer of memory foam, to prevent the absorption of water. The strap assembly is configured to support the arm support cushion to position and support the wearer's arm at a prescribed angle of abduction, extension, and/or rotation. A quick release coupling may be used to secure each of the ends of the strap assembly to the arm support cushion.

BRIEF DESCRIPTION OF THE DRAWINGS

The description of the various example embodiments is explained in conjunction with appended drawings, in which.

DETAILED DESCRIPTION OF THE INVENTION

As used throughout this specification, the word "may" is used in a permissive sense (i.e., meaning having the potential to), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that citing herein of any patents, published patent applications, and non-patent literature is not an admission as to any of those references constituting prior art with respect to the disclosed and/or claimed apparatus/method.

Furthermore, any reference made throughout this specification to "one embodiment" or "an embodiment" means that a particular feature, structure or characteristic described in connection therewith is included in at least that one particular embodiment. Thus, the appearances of the phrases "in one embodiment" or "in an embodiment" in various places throughout this specification are not necessarily all referring to the same embodiment. Therefore, the described features, advantages, and characteristics of any particular aspect of an embodiment disclosed herein may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/feature being quantified. Furthermore, a numerical difference provided by the approximating language may also correspond to an overall tolerance for the aspect/feature that may be derived from variations resulting from a stack up (i.e., the sum) of a multiplicity of such individual tolerances.

Any use of a friction fit (i.e., an interface fit) between two mating parts described herein indicates that the opening (e.g., a hole) is smaller than the part received therein (e.g., a shaft), which may be a slight interference in one embodiment in the range of 0.0001 inches to 0.0003 inches, or an interference of 0.0003 inches to 0.0007 inches in another embodiment, or an interference of 0.0007 inches to 0.0010 inches in yet another embodiment, or a combination of such ranges. Other values for the interference may also be used in different configurations (see e.g., "Press Fit Engineering and Design Calculator," available at: www.engineersedge.com/calculators/machine-design/press-fit/press-fit-calculator.htm).

Any described use of a clearance fit indicates that the opening (e.g., a hole) is larger than the part received therein (e.g., a shaft), enabling the two parts to move (e.g. to slide and/or rotate) when assembled, where the gap between the opening and the part may depend upon the size of the part and the type of clearance fit—i.e., loose running, free running, easy running, close running, and sliding (e.g., for a 0.1250 inch shaft diameter the opening may be 0.1285 inches for a close running fit, and may be 0.1360 inches for a free running fit; for a 0.5000 inch diameter shaft the opening may be 0.5156 inches for a close running fit and may be 0.5312 inches for a free running fit). Other clearance amounts are used for other clearance types. See "Engineering Fit" at: https://en.wikipedia.org/wiki/Engineering_fit; and "Three General Types of Fit," available at www.mm-to.org/dclark/Reports/Encoder %20Upgrade/fittolerences%20%5BRead-Only%5D.pdf.

For certain injuries, a patient is required to wear a shoulder sling to immobilize his/her arm which often includes a particularly shaped elevation support cushion to immobilize the limb at a particular angle to the wearer's body—i.e., a particular abduction, extension, and/or rotation angle.

Figure 1:
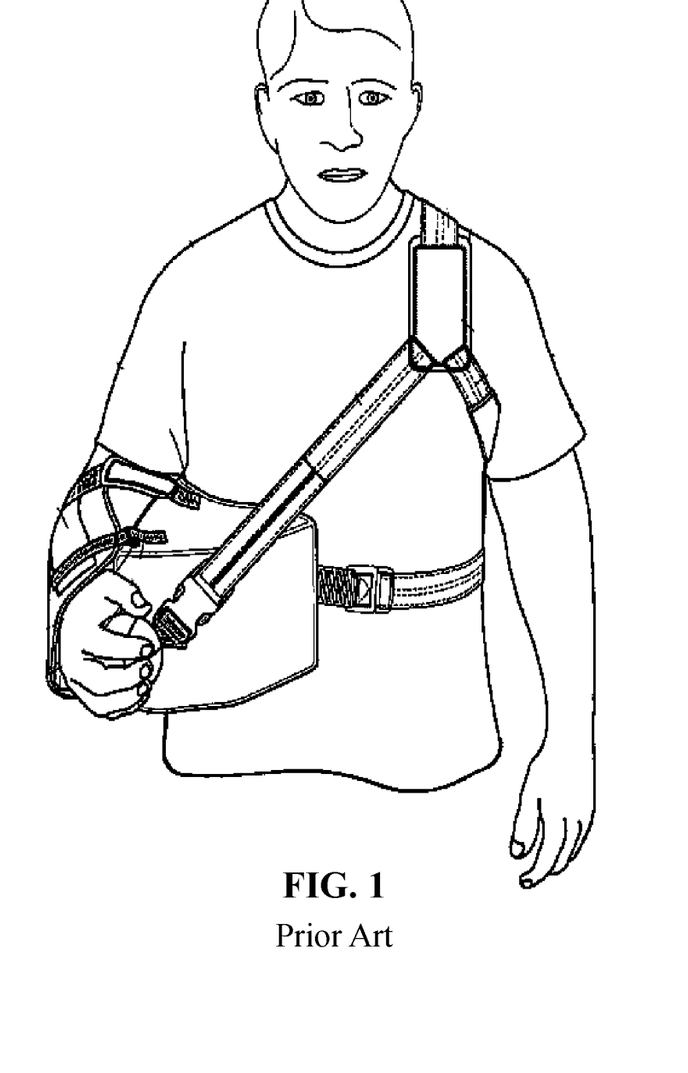
FIG. 1 is a prior art shoulder sling with a support cushion.
Figure 2:
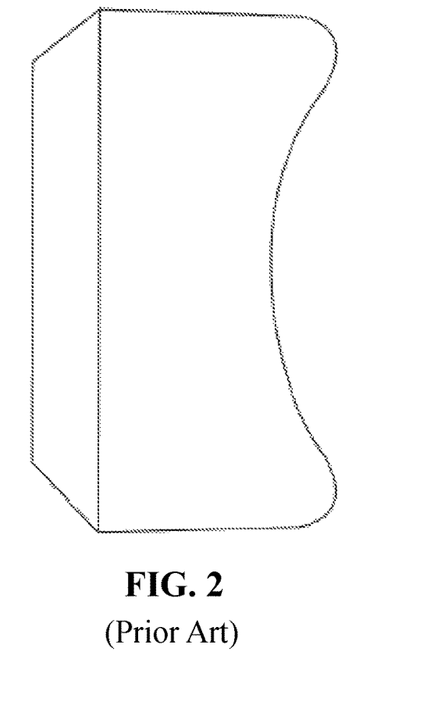
FIG. 2 is a side view of a prior art foam cushion for use with a shoulder sling.

FIGS. 3-7 shows a sling 100 that includes a cushion formed as an air-filled bladder 100B that may have an exterior shaped the same as a prior art foam cushion, but which is about 1/10$^{th}$ of its weight. The air-filled bladder 100B may look the same on the outside as the prior art foam cushion, and may perform the same or even better. The expandable air-filled bladder 100B replaces the heavy, hot, space-consuming foam utilized as a cushion in prior art shoulder slings (see e.g., FIGS. 1-2), which air-filled bladder is also collapsible to minimize volume when not in use, and which may also add several other useful features and elements in various embodiments. The air-filled bladder 100B is water-proof, repelling water, and thus does not absorb water like the prior art foam cushion, as it is water resistant and will not become water laden and heavy when the user may be caught out in the rain. The user may also therefore wear the sling 100 with air-filled bladder cushion 100B disclosed herein while in the shower.

The air-filled bladder cushion 100B may be formed with a first side 101 that may be contoured to correspond to the shape of, and comfortably rest against (i.e., butt against) the torso of the wearer, and a second side 102 that may be contoured to correspond to and support the wearer's arm, which sides may be connected by at least third and fourth side surfaces 103/104. The sling 100 may also be formed with at a strap assembly 105 that may be adjustable in length, to accommodate different sized wearer's, and which may have straps that may be placed over the wearer's shoulder and under the corresponding arm. One or both ends of the strap assembly 105 may have a buckle 105Bi configured to releasably attach in a quick release manner to a mating buckle member 105Bii secured to the cushion (see FIG. 4). It will be understood by those of skill in this art that in combination with the sling, the particular size and shape of those contoured surfaces, particularly surfaces 101/102, and the positioning of the ends of the strap 105 and the length(s) and positioning of the strap(s) on the sling, will all be coordinated to provide a desired position of abduction, extension, and/or rotation of the wearer's arm.

Figure 3:
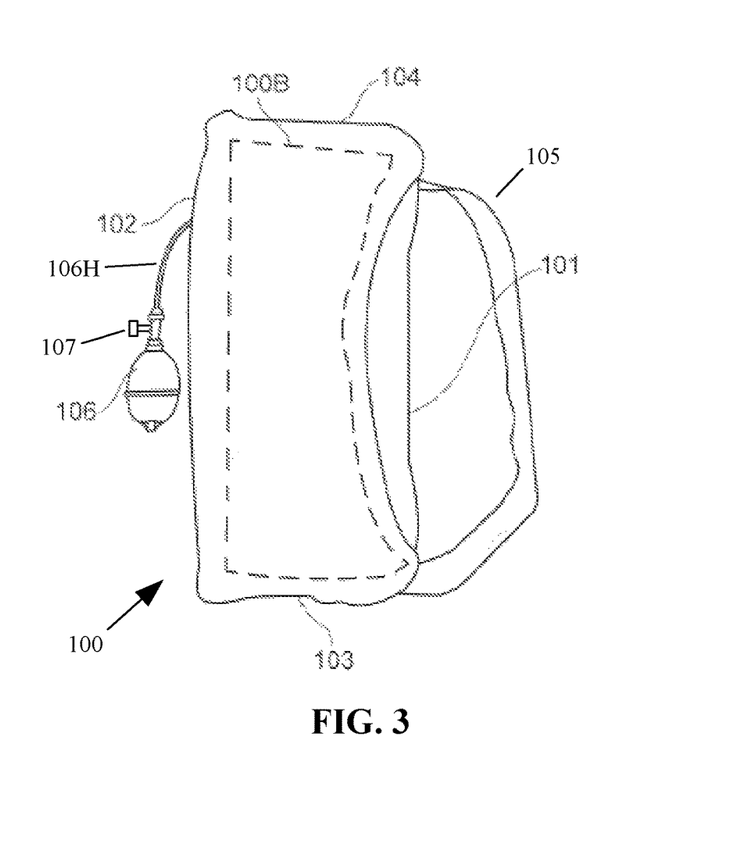
FIG. 3 is a side view of a sling with an air-filled bladder as disclosed herein, usable for providing light-weight abduction, extension, and/or rotation angle positioning of the wearer's limb while being supported by a wearer's shoulder, and with the air-filled cushion shown without a cloth outer covering.
Figure 4:
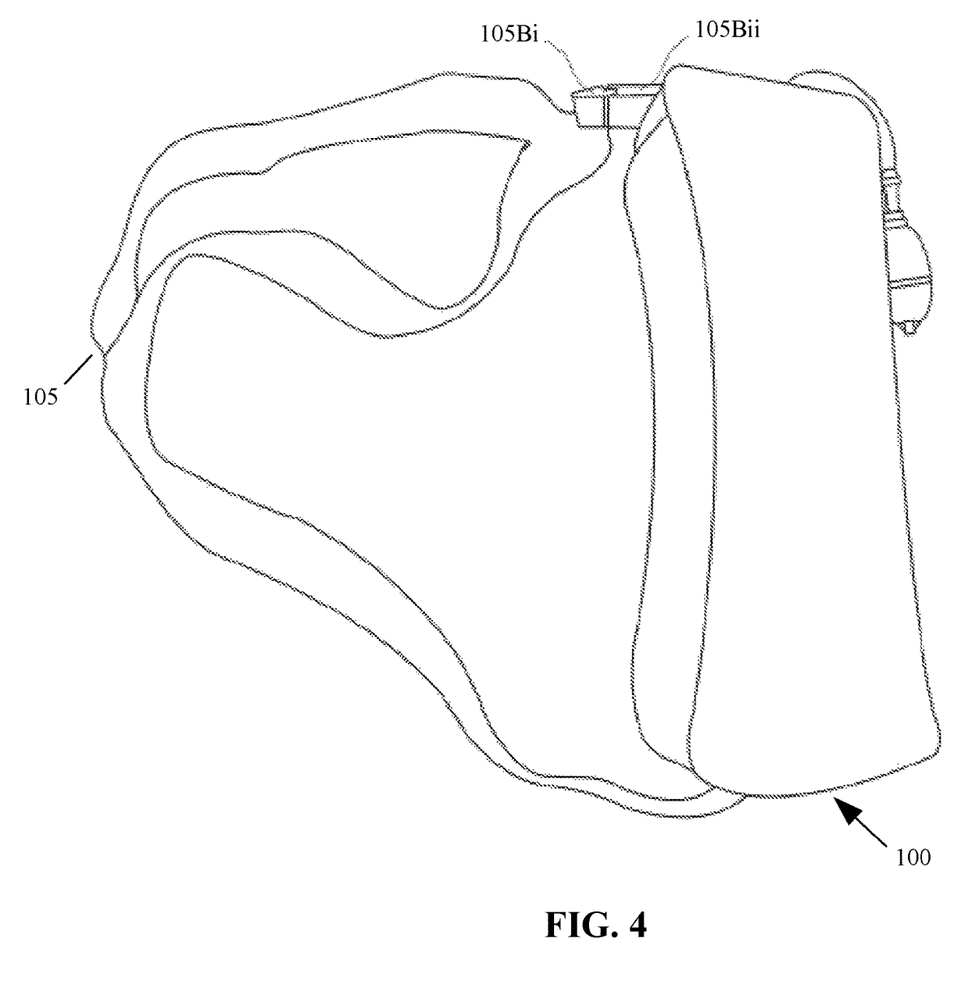
FIG. 4 is a first perspective view of the sling of FIG. 3.

In one embodiment, as may be seen in FIG. 3, the sling 100 may have exterior padding added onto one or more portions of the air-filled bladder 100B, particularly on the first and second surfaces 101 and 102, to provide added comfort for the wearer's torso and arm, which padding may preferably be a thin layer of memory foam (e.g., 0.25 inches to 1.0 inches of memory foam). This added memory foam may serve to better conform those surfaces locally to the wearer's individual contours. The surface that include a thin foam layer may also be covered with a water resistant material to prevent absorption of water by the padding, despite its small thickness/volume.

In another embodiment, the interior of the bladder 100B, which may be waterproof, may include a layered high elastic/expansion foam, which may suck air into the bladder to the point of being about 85% filled to capacity, after an air valve has been opened. The suction created by the interior foam in this embodiment serves to greatly increase the speed of inflation when the person desires to use the sling 100.

The bladder 100B may be fully inflated to 100 percent of its design capacity, for either embodiment (i.e., with or without the high expansion foam being contained inside the bladder), by using a suitable pump. In one embodiment, the pump may be a resilient bulbous hand pump 106 (see e.g., U.S. Pat. Nos.: 795,108 to Doellinger; U.S. Pat. No. 3,411, 164 to Sumergrade; U.S. Pat. No. 3,633,567 to Sarnoff; and U.S. Pat. No. 5,628,721 to Arnold). The resilient bulb of pump 106 may be in fluid communication with the bladder 100B through a valve 107 and a hose 10611. The valve 107 may be rotated (e.g., rotated counter-clockwise) to be opened to release air from the bladder, when the user desires to collapse it for storage in a small place, such as a drawer. The valve 107 may alternatively be counter-rotated (e.g., rotated clockwise) to be closed, so that the air supplied into the bladder by squeezing of the resilient bulb will be contained within, and serve to inflate, the bladder, when the user desires to use the sling 100.

Figure 5:
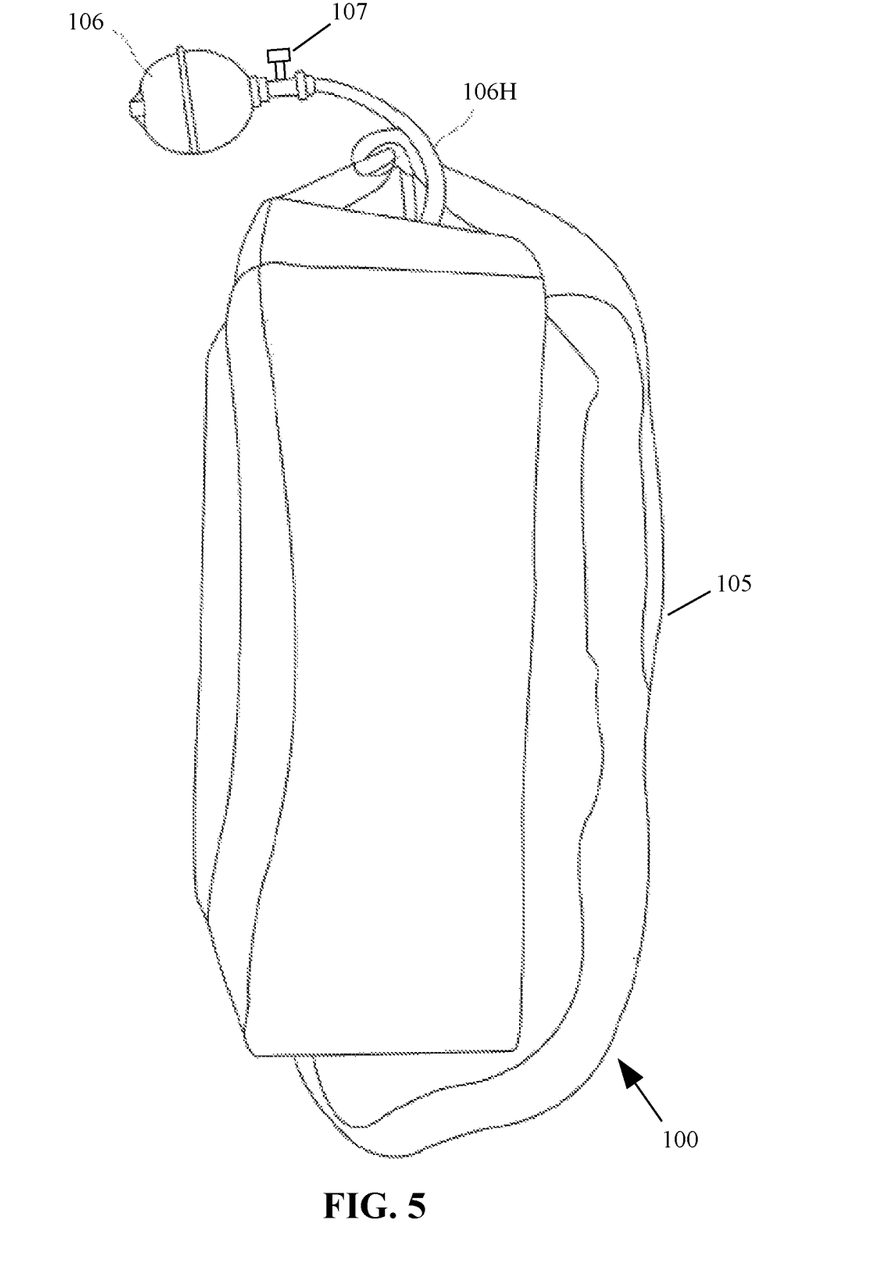
FIG. 5 is a second perspective view of the sling of FIG. 3.
Figure 5A:
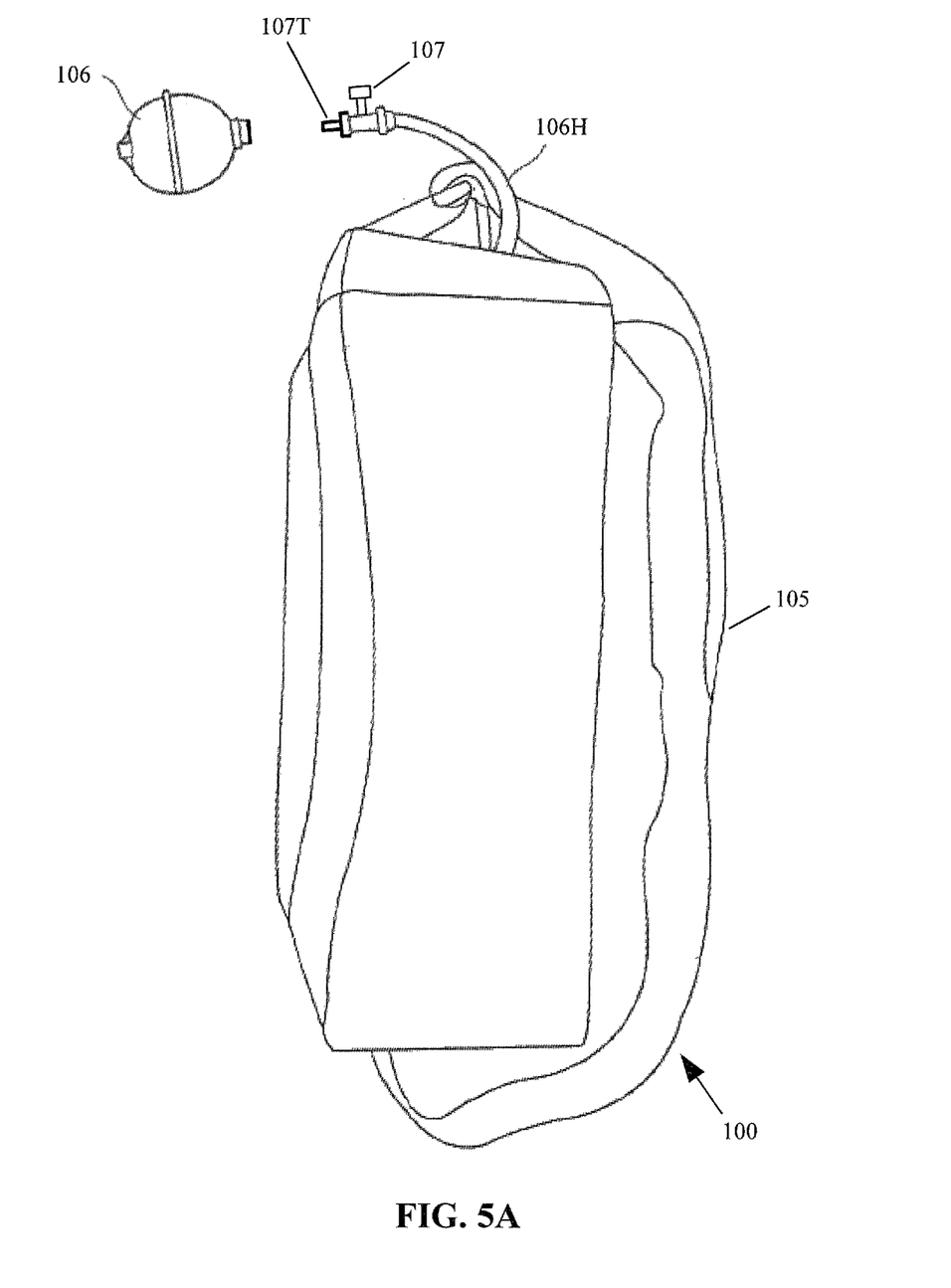
FIG. 5A is the perspective view of FIG. 5, but shown with the bulbous hand pump decoupled from the valve of the hose.
Figure 6:
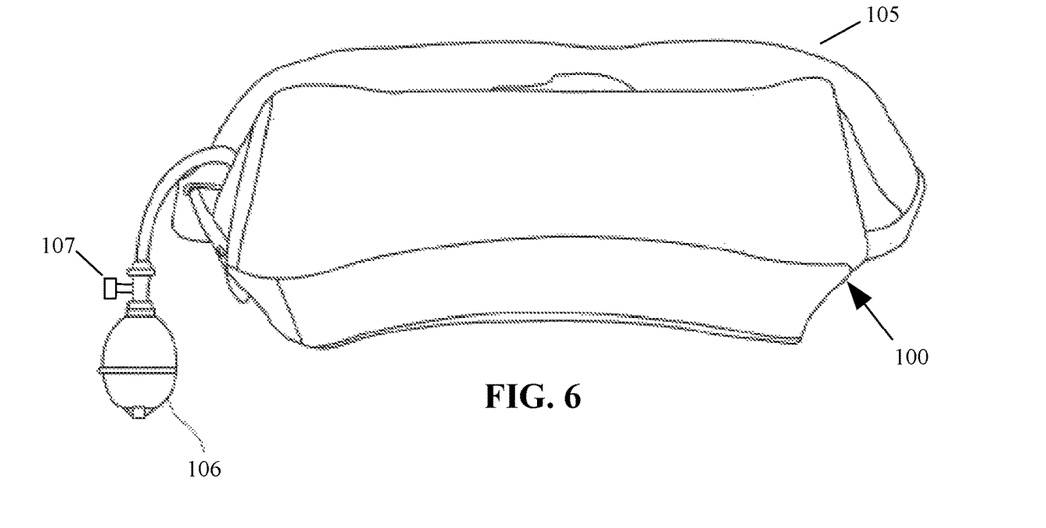
FIG. 6 is a third perspective view of the sling of FIG. 3.

As seen in FIG. 5A, the bulb-shaped hand pump 106 may be configured to releasably couple to a threaded portion 107T of the valve 107 of the hose 10611 that is in fluid communication with the bladder 100B. The bulb-shaped hand pump 106 may typically be detached so that the wearer of the device, after inflation had been completed, may also be able to utilize the resilient hand pump like a ball that is typically squeezed to exercise the arm muscles. In addition, the detached resilient bulb-shaped hand pump 106 may be squeezed to blow cooling air onto the wearer's support arm, which tends to become hot and sweaty, particularly when it is maintained in a cast. The resilient bulb-shaped hand pump 106 may be made of natural or synthetic rubber, or any other suitable material.

Figure 7:
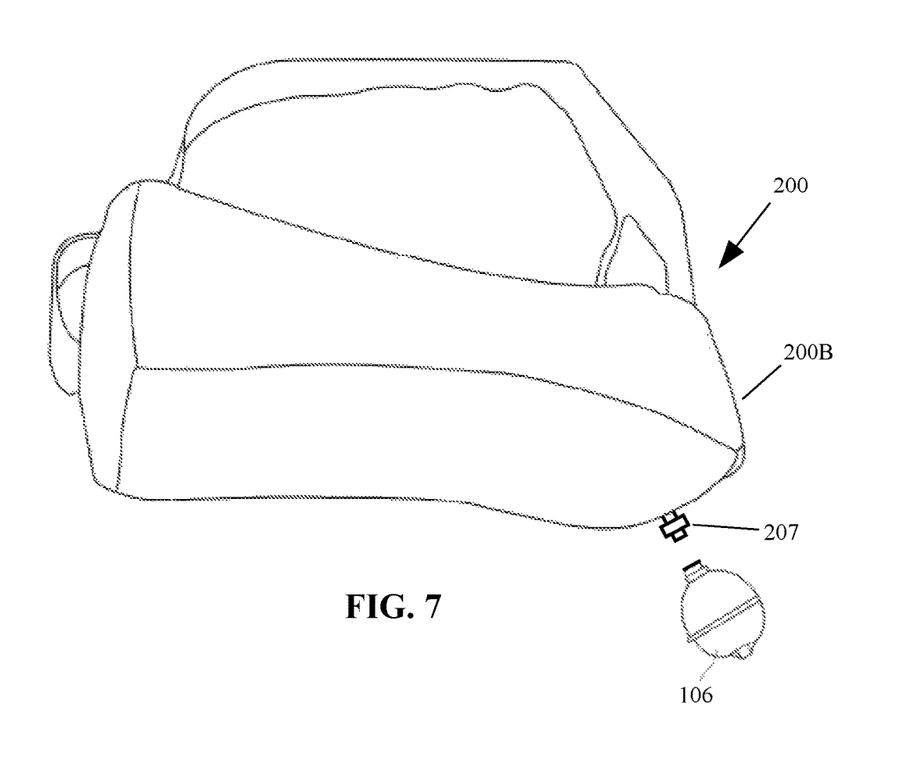
FIG. 7 shows a perspective view of another sling embodiment.

In another embodiment, shown for sling 200 in FIG. 7, an air-fillable bladder 200B may have one resilient hand pump 106 releasably coupled to a low-profile valve 207 (see e.g., U.S. Pat. No. 6,460,560 to Weinheimer for "Low Profile Inflation Valve"), thereby being in fluid communication with the bladder without the use of a hose.

Figure 8:
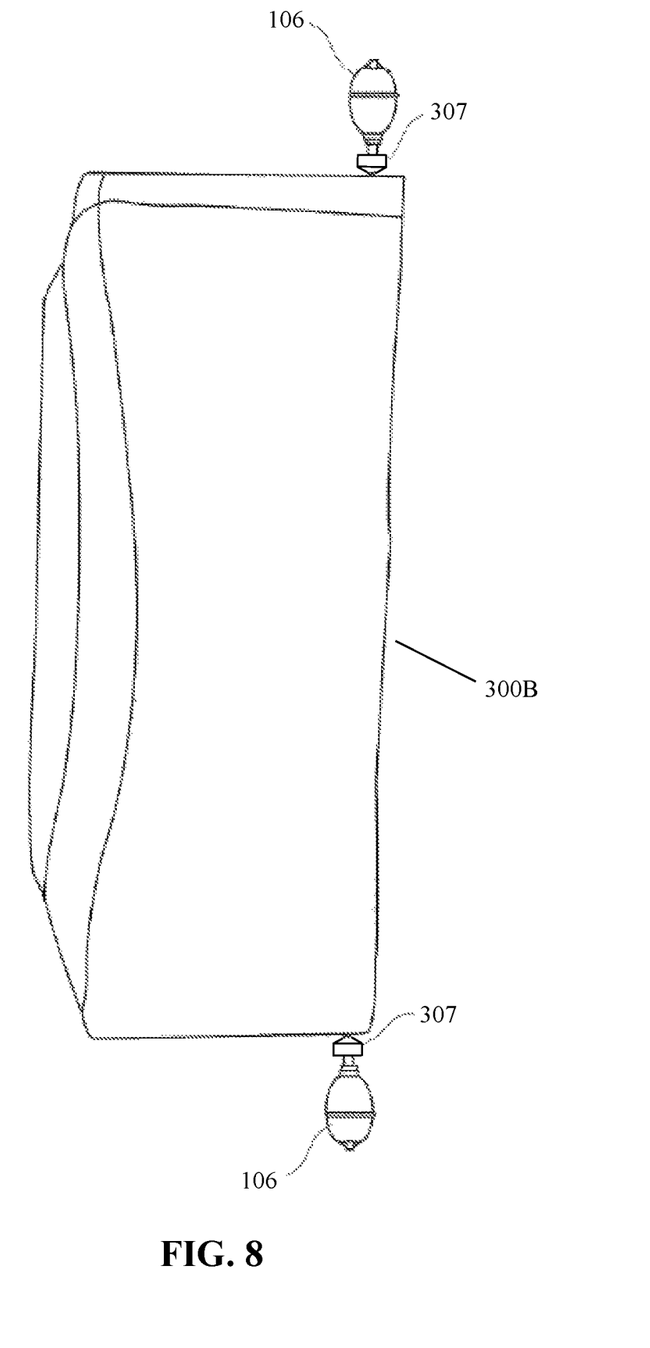
FIG. 8 shows an alternate embodiment of the air-filled bladder usable for the sling disclosed herein, in which a resilient hand pump and a valve are attached to the cushion without the use of a hose, and a pair of valves/pumps may be attached on opposite sides of the cushion to provide for universal use, being either left-handed or right-handed use.
Figure 9:
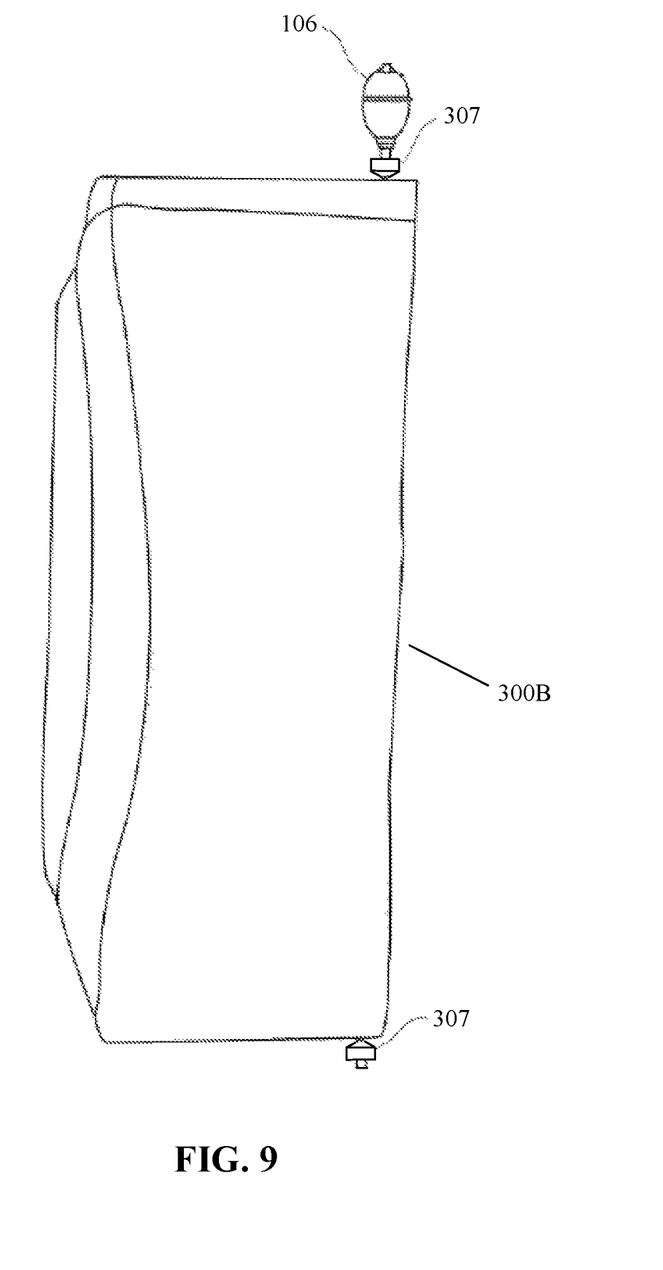
FIG. 9 shows the air-filled bladder as seen in FIG. 8, but is shown with only a single resilient hand pump releasably attached to one of the two valves.

In a yet another embodiment, shown in FIG. 8, an air-fillable bladder 300B may have a pair of resilient hand pumps 106 releasably coupled to respective low profile valves 307, with one valve/pump combination being positioned on each side of the bladder to provide for universal use, being either left-handed or right-handed use. The air-filled bladder 300B may alternatively be utilized with only a single resilient hand pump 106 that may be releasably attached (e.g., by being threaded) to either valve to provide for universal use, being either left-handed or right-banded use, depending upon the user.

The air-fillable bladder 100B/200B/300B may be deflated and be stored in a hangable box along with the sling, occupying a small volume compared with the prior art sling that uses a foam cushion.

Figure 10:
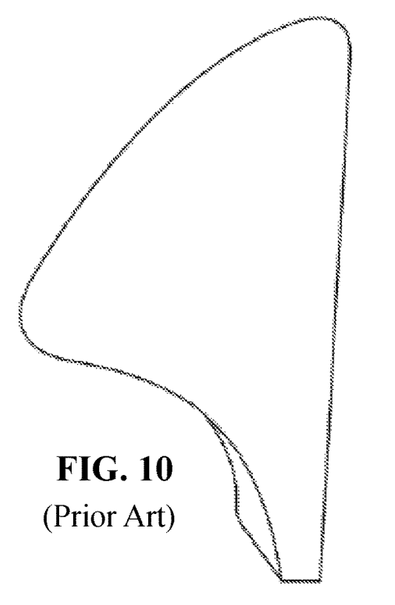
FIG. 10 is a side view of another prior art foam cushion for use with a shoulder sling.
Figure 11:
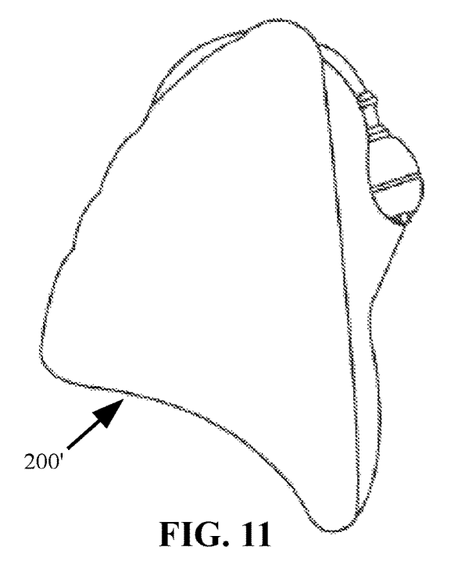
FIG. 11 is a side view of a another embodiment of an air-filled abduction cushion as disclosed herein, being shaped the same as the prior art foam cushion shown in FIG. 10, and being shown without a cloth outer covering.
Figure 12:
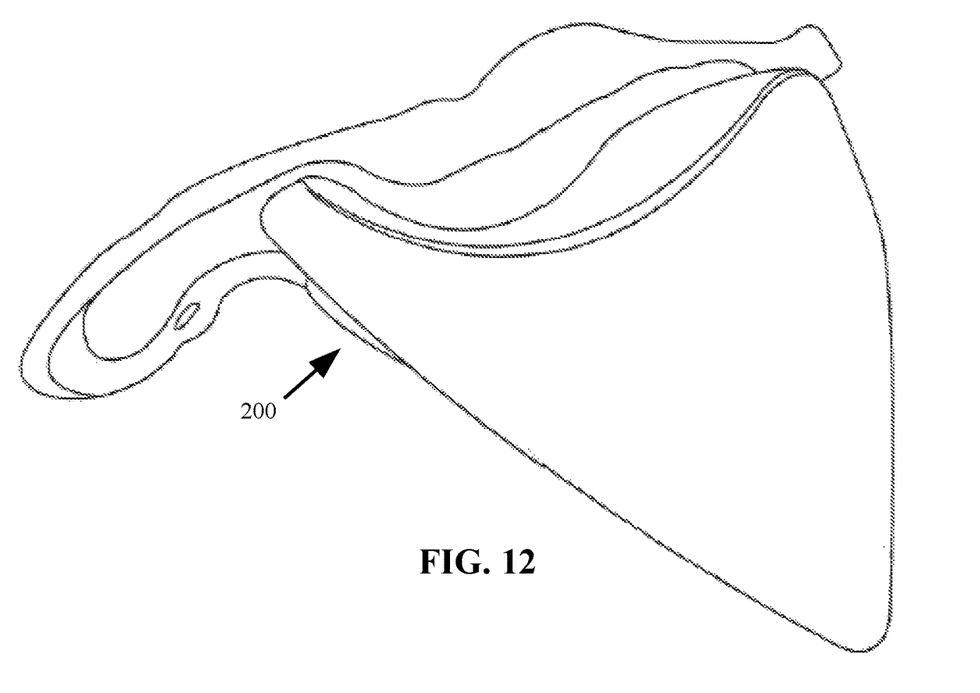
FIG. 12 is the air-filled abduction cushion shown in FIG. 11, being shown with a fabric outer covering and a strap arrangement.

FIG. 10 shows an air-filled cushion 400, also usable for providing light-weight abduction, extension, and/or rotation angle positioning of the wearer's limb while being supported by a shoulder sling, and being shown without a cloth outer covering. The air-filled cushion 400 may be shaped to provide different angular support for the wearer's arm.

While illustrative implementations of one or more embodiments of the disclosed apparatus are provided hereinabove, those skilled in the art and having the benefit of the present disclosure will appreciate that further embodiments may be implemented with various changes within the scope of the disclosed apparatus. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

I claim:

1. A sling, for use in supporting a wearer's arm, said sling comprising:
    an arm support cushion, said arm support cushion comprising:
        an inflatable bladder, said inflatable bladder comprising: a first surface adapted to correspond to the contour of, and butt against, the wearer's torso; and a second surface adapted to correspond to the contour of, and support, the wearer's arm; wherein said inflatable bladder is of a one-piece construction;
        a valve, said valve configured for actuation into a first position to only permit air flow in a first direction though said valve, being into said inflatable bladder, and for actuation into a second position to only permit air flow through said valve in a second direction, being out of said inflatable bladder; said valve comprising a threaded portion;
        a hand-squeezable pump configured to inflate said inflatable bladder without the use of a hose when squeezed;
    a strap assembly, said strap assembly configured to support said arm support cushion to position and support the wearer's arm at a prescribed angle of abduction, extension, and/or rotation;
    wherein said hand-squeezable pump comprises a resilient, bulb-shaped pump;
    wherein said hand-squeezable pump is configured to releasably couple to said threaded portion of said valve, to permit decoupling of said resilient, bulb-shaped pump and further permit one or more of: exercising by the user by squeezing of said resilient, bulb-shaped pump, and blowing of air by the user onto the arm supported by said sling by squeezing of said resilient bulb-shaped pump;
    wherein said valve is positioned on a first side of said inflatable bladder, and being adapted for left-handed use of said hand-squeezable pump by the wearer; and
    wherein said arm support cushion comprises a second said valve, said second valve positioned on a second side of said inflatable bladder, and being adapted for right-handed use of said hand-squeezable pump by the wearer.

2. The sling according to claim 1, wherein said inflatable bladder comprises a first layer of memory foam on said first surface, and a second layer of memory foam on said second surface, said first surface and said second surface thereby adapted to better conform to the respective contours of the wearer.

3. The sling according to claim 2, further comprising a first piece and a second piece of water resistant material positioned to respectively overlie said first layer of memory foam and said second layer of memory foam.

4. The sling according to claim 1 wherein said resilient, bulb-shaped pump is made of rubber.

5. The sling according to claim 1, wherein said valve is a low profile inflation valve configured for releasable attachment of said resilient bulb-shaped pump.

6. The sling according to claim 1, where said inflatable bladder further comprises: high-inflation foam in an interior of said inflatable bladder, said high-inflation foam configured to suck air into said inflatable bladder to increase a rate of inflation of said inflatable bladder from a deflated condition.

7. The sling according to claim 1, further comprising: means for releasably coupling each of a first end and a second end of said strap assembly to said arm support cushion.

8. The sling according to claim 1, wherein said inflatable bladder comprises a cloth outer covering.

* * * * *